(12) United States Patent
Scheibel et al.

(10) Patent No.: US 8,721,991 B2
(45) Date of Patent: May 13, 2014

(54) MICROFLUIDIC DEVICE FOR CONTROLLED AGGREGATION OF SPIDER SILK

(75) Inventors: Thomas Scheibel, Bayreuth (DE); Daniel Huemmerich, Frankenthal (DE); Sebastian Remmensee, Munich (DE); Christian Freudiger, Pullach (DE); Andreas Bausch, Munich (DE)

(73) Assignee: AMSilk GmbH, Planegg/Martinsried (DE)

( * ) Notice: Subject to any disclaimer, the term of this patent is extended or adjusted under 35 U.S.C. 154(b) by 1200 days.

(21) Appl. No.: 12/227,498

(22) PCT Filed: May 21, 2007

(86) PCT No.: PCT/EP2007/054878
§ 371 (c)(1),
(2), (4) Date: Jul. 10, 2009

(87) PCT Pub. No.: WO2007/141131
PCT Pub. Date: Dec. 13, 2007

(65) Prior Publication Data
US 2010/0029553 A1    Feb. 4, 2010

(30) Foreign Application Priority Data
Jun. 8, 2006    (EP) .................... 06011841

(51) Int. Cl.
B01L 3/00    (2006.01)
(52) U.S. Cl.
USPC .......................................... 422/502
(58) Field of Classification Search
USPC .......................................... 422/502
See application file for complete search history.

(56) References Cited

U.S. PATENT DOCUMENTS

| 2004/0086591 A1* | 5/2004 | Vollrath et al. ............... 425/143 |
| 2004/0102614 A1 | 5/2004 | Islam et al. |
| 2010/0013115 A1* | 1/2010 | Breslauer et al. ............. 264/130 |

FOREIGN PATENT DOCUMENTS

| WO | WO 2005/017237 | 2/2005 |
| WO | WO 2006/002827 | 1/2006 |
| WO | WO 2007/031301 | 3/2007 |

OTHER PUBLICATIONS

International Search Report corresponding to International Application No. PCT/EP2007/054878 dated Dec. 9, 2007.
Beebe et al., "Physics and Applications of Microfluidics in Biology," Annu. Rev. Biomed. Eng., vol. 4, pp. 261-286 (2002).
Breslauer, D., "Biologically-inspired Microfluidic Silk Spinning," A proposal submittedfor the 2007 Bears Breaking Boundaries Contest (XP-002448394).
Lazaris et al., "Spider Silk Fibers Spun from Soluble Recombinant Silk Produced in Mammalian Cells," Science, vol. 295, pp. 472-476 (Jan. 18, 2002).
Rammensee et al., "Recombinantly Produced Spider Silk in a Microfluidic Device," German Physical Society Conference (2007) (Abstract).
Seidel et al., "Artificial Spinning of Spider Silk," Macromolecules, vol. 31., pp. 6733-6736 (1998).
Weigl et al., "Standard and high-throughput microfluidic disposables based on laminar fluid diffusion interfaces," Proceedings of SPIE, vol. 4626, pp. 421-428 (2002).

* cited by examiner

Primary Examiner — Walter D Griffin
Assistant Examiner — Christopher K Vandeusen
(74) Attorney, Agent, or Firm — Faegre Baker Daniels LLP

(57) ABSTRACT

The present invention is directed to a device and method of controlling the phase separation of one or a mixture of two or more spider silk proteins, leading to the defined and controllable assembly of the said silk protein(s) to defined morphologies, such as spheres, nano fibrils, threads, etc.

6 Claims, 7 Drawing Sheets

MICROFLUIDIC DEVICE FOR CONTROLLED AGGREGATION OF SPIDER SILK

The present invention is directed to a device and method of controlling the phase separation of one or a mixture of two or more spider silk proteins, leading to the defined and controllable assembly of the said silk protein(s) to defined morphologies, such as spheres, nanofibrils, threads, etc.

STATE OF THE ART

Spider silks are protein polymers that display extraordinary physical properties. Among the different types of spider silks, draglines are most intensely studied. Dragline silks are utilized by orb weaving spiders to build frame and radii of their nets and as lifelines that are permanently dragged behind. For these purposes high tensile strength and elasticity are required. The combination of such properties results in a toughness that is higher than that of most other known materials. Dragline silks are generally composed of two major proteins whose primary structures share a common repetitive architecture.

An orb web's capture spiral, in part composed of viscid silk formed by the flagelliform gland, which is therefore named flagelliform silk, is stretchy and can triple in length before breaking, but provides only half the tensile strength of dragline silk.

Variations of a single repeat unit, which can comprise up to 60 amino acids, are iterated several times to represent the largest part of a dragline spider silk sequence. These repeat units comprehend a limited set of distinct amino acid motifs. One motif found in all dragline silk repeat units is a block of typically 6-9 alanine residues. In silk threads several polyalanine motifs form crystalline β-sheet stacks leading to tensile strength.

Glycine rich motifs such as GGX or GPGXX adopt flexible helical structures that connect crystalline regions and provide elasticity to the thread.

Silk assembly in vivo is a remarkable process, Spider dragline silk proteins are stored at concentrations up to 50% (w/v) in the so-called major ampullate gland. Although a "dynamic loose helical structure" has been proposed for the proteins within the major ampullate gland more recent data suggests a random coil conformation for the proteins of the so called A-Zone, which represents the largest part of the gland. The highly concentrated protein solution forms the silk dope (spinning solution), which displays properties of a liquid crystal.

Thread assembly is initiated during a passage of the dope through the spinning duct accompanied by extraction of water, sodium and chloride. At the same time the concentrations of the more lyotropic ions potassium and phosphate are increased and the pH drops from 6.9 to 6.3. Assembly is finally triggered by mechanical stress, which is caused by pulling the thread out of the spider's abdomen.

For several purposes natural silk threads can not be used directly, but have to be dissolved and reassembled into other morphologies such as films, foams, spheres, nanofibrils, hydrogels and the like.

While some structural aspects of spider silk proteins have been unravelled, still little is known about the contribution of individual silk proteins and their primary structure elements to the assembly process. Comparative studies of the two major dragline silk proteins of the garden spider *Araneus diadematus*, ADF-3 and ADF-4, revealed that, although their amino acid sequences are rather similar, they display remarkably different solubility and assembly characteristics: While ADF-3 is soluble even at high concentrations, ADF-4 is virtually insoluble and self-assembles into filamentous structures under specific conditions (unpublished results).

Scientific and commercial interest initiated the investigation of industrial scale manufacturing of spider silk. Native spider silk production is impractical due to the cannibalism of spiders, and artificial production has encountered problems in achieving both sufficient protein yield and quality thread-assembly. Bacterial expression yielded low protein levels, likely caused by a different codon usage in bacteria and in spiders. Synthetic genes with a codon usage adapted to the expression host led to higher yields, but the proteins synthesized thereof showed different characteristics in comparison to native spider silks. Expression of partial dragline silk cDNAs in mammalian cell lines did yield silk proteins (e,g. ADF-3) that could be artificially spun into 'silken' threads, albeit as yet of inferior quality.

Two of the inventors earlier developed systems for the recombinant production of spider silk proteins in *E. coli*. As an example, it is referred to WO 2006/008163 incorporated herein in its entirety by reference. In this expression system, single building blocks (=modules) can be varied freely and can thus be adapted to the requirements of the specific case, Modules of this type are disclosed also in Hümmerich, D., Helsen, C. W., Oschmann, J., Rudolph, R. & Scheibel, T. (2004): "Primary structure elements of dragline silks and their contribution to protein solubility and assembly, *Biochemistry* 43, 13604-13612".

Microfluidics—fluid flow in laminar regime—have been used in the context of protein polymerization by different groups. Nevertheless, microfluidics have not been associated with the polymerization of spider-silk proteins. The only cases in which they and proteins appear in literature together are, when a surface is coated with proteins in certain shapes. In the proposed approach the polymerization takes place in the lumen of the channel.

As microfluidics have many applications, both in science and in industry, the technique is very advanced. For developing the microfluidic devices used in the process described here, fast prototyping in PDMS as detailed in [6] and depicted in FIGS. 2 and 3 was applied. Short times from prototyping on PC to completion and the ability to use light-microscopy are the main advantages of building microfluidic devices in PDMS. For later industrial use, devices that are more resistible could easily built by existing methods—thus only defined (laminar) flow conditions have to be realized.

As an example for the production of microfluidic devices, it is referred to FIG. 1 (see [6]). A scheme for rapid prototyping and replica molding of microfluidic devices in PDMS is described. The steps comprise the following:

A design of a channel is created in a CAD program.

This file is printed with a Linotronic 300 printer on a high-resolution transparency with a resolution of 3048 dpi and serves as a positive-film (A)

A plane silicon wafer is coated with SU8-100. The transparency then serves as the photo mask for lithography (B).

Dissolving away the unpolymerized photo resist leaves a positive relief that serves as a master for later PDMS cast (C).

As an additional example, it is referred to FIG. 2 (see [6]): The scheme is describing replica molding of microfluidic devices comprising the steps of:

A master is fabricated by rapid prototyping like described above (A).

Posts are placed on the master to define reservoirs. It is also possible to already put the inlets and outlets in place (B).

The prepolymer is cast on the master and cured (C).

The PDMS replica is removed form the master after 1 h @ 80° C. (D).

Exposing the replica and a glass-slide to an air plasma and placing the two surfaces in conformal contact makes a tight, irreversible seal (E).

However, the methods for producing assembled proteins, threads etc. from spider silk proteins which are known up to now, suffer from several disadvantages which do not allow to produce said materials in a sufficiently high quantity and quality.

For example, Liivak et al., 1998 describe such a method, wherein silk proteins of *Nephila clavipes* dissolved in Hexafluoroisopropanol were used as starting material. The dissolved proteins were injected into a precipitation bath (acetone) through a nozzle. The threads obtained by said method, however, were brittle and did not resemble the natural spider silk threads very much.

Another group developed a spinning method, wherein water/methanol was used as precipitation bath. However, also these threads turned out to be brittle (Arcidiacono et al., 2002).

Further methods were disclosed by Lazaris et al., 2002, and in US 2003/0201560, WO 2005/017237, and WO 2004/057069.

Furthermore, up to now, no satisfying technique for coupling is known which allows on the one hand a coupling of those substances to spider silk proteins in a predetermined amount and, on the other hand, to predetermined locations within the spider silk protein.

Thus, there is still a need to provide improved methods for producing products of assembled spider silk proteins.

Therefore, it is an object of the present invention to provide an improved device and process for producing threads, filaments and the like from spider silk proteins, allowing a continuous production of high quality products made from spider silk proteins. It is a further object underlying the present invention to provide a method for the manufacture of modified spider silk proteins which can be used for the targeted coupling of substances such as drugs, metals, polypeptides, polysaccharides, marker molecules, quantum dots, nucleic acids, lipids, etc. to these spider silk proteins. It is a further object of the invention to provide such modified spider silk sequences which can be used to carry and deliver a precise amount of those substances and wherein those substances are coupled in predetermined locations within the sequence of the spider silk protein.

These and further objects are solved by the subject-matter of the independent claims. Preferred embodiments are set forth in the dependent claims.

To solve the problem of phase separation of designed and recombinantly produced silk proteins, the present invention provides a technique which combines existing methods described above and evades their disadvantages.

Figure 1:
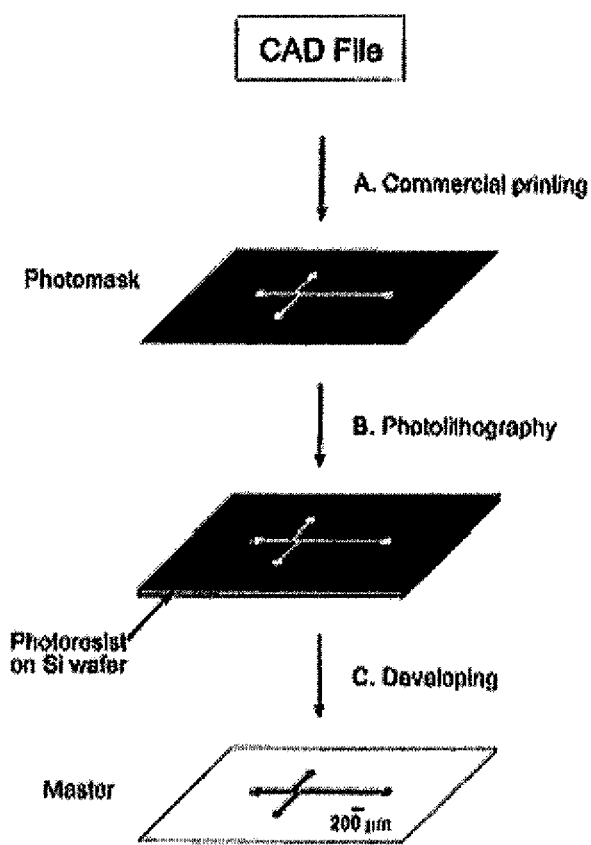
FIG. 1. Steps of producing microfluidic devices.
Figure 2:
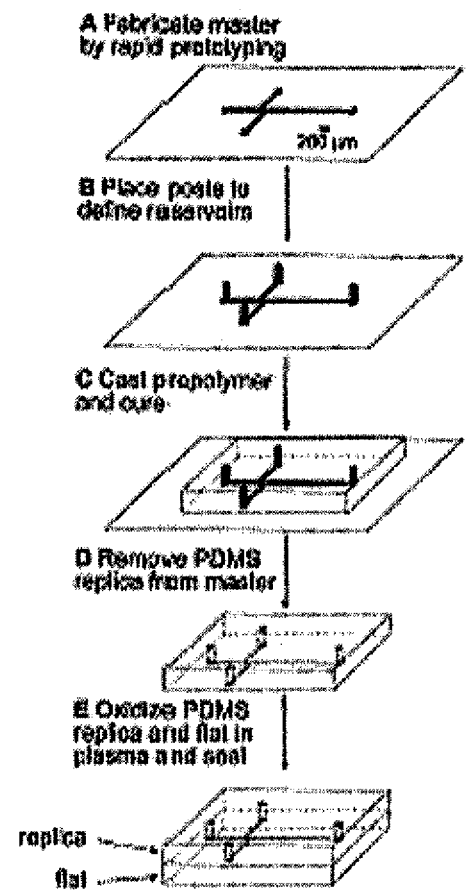
FIG. 2. Fast prototyping in Plant Design Management Software to develop the microfluidic devices.
Figure 3:
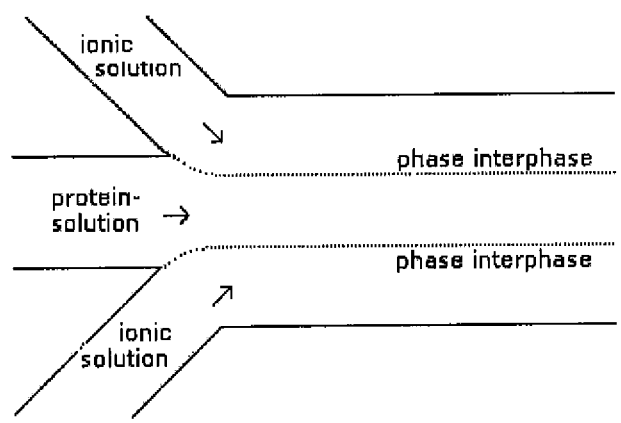
FIG. 3. A schematic essay of the microfluidic device comprising a plurality of microfluidic channels.

As an example of the device of the present invention, a device as shown in FIG. 3 and constructed as described above was built: In a microfluidic junction three liquid flows meet and run parallel to the outlet on the right. In first experiments the inner channel was filled with a solution of bacterially produced spider silk protein and both outer channels with a solution containing phosphate-ions.

FIG. 3 shows a schematic essay of the microfluidic device used in the experiment described above.

In particular, the present invention is directed to the following aspects and embodiments:

According to first aspect, the invention provides a microfluidic device comprising:

a) at least three microfluidic channels formed in said device for flowing fluids therethrough, wherein the channels converge in said microfluidic device to one combined channel in order to provide a laminar flow of said fluids, said combined channel leading to an outlet port;

b) at least three inlet ports formed in said device to permit access to the at least three microfluidic channels; and c) at least three storage means for fluids, each being connected via said inlet ports to one of the at least three microfluidic channels, characterized in that at least one of said storage means comprises a solution of one or more spider silk proteins and at least one of said storage means comprises a ionic solution.

In other words, the device may also comprise a plurality of storage means and the respective microfluidic channels, for example several containers containing different protein solutions etc.

According to a preferred embodiment, the ionic solution is comprising lyotropic ions, preferably potassium and/or phosphate ions. Those ions are serving as aggregation trigger for aggregating the spider silk proteins. Other triggers are acidification, preferably to a pH of about 1, and mechanical stress, preferably applying shearing forces which are a direct result of the arrangement of the present device.

As it can be seen from FIG. 3, the microfluidic device of the present invention comprises a plurality of microfluidic channels formed in said device for flowing fluids therethrough, wherein the channels converge in said microfluidic device to one combined channel (at one predetermined point) in order to provide a laminar flow of said fluids. This laminar flow produces shear forces required for thread assembly.

The solution of spider silk proteins used in the present invention also is called "dope" solution. It may contain all types of spider silk proteins, e.g. the synthetic silk proteins and/or authentic silk proteins from one or more spider species, or silk proteins from different silk-producing genera, for example, a mixture of silk proteins from spiders and *B. mori*. In the most preferred embodiments, the silk proteins are dragline and/or flagelliform silks from *N. clavipes* or *A. diadematus*, particularly the proteins MaSpI, MaSpII, ADF-3, ADF-4 and Flag. In alternative embodiments, the dope solution contains a mixture of silk proteins and one or more synthetic polymers or natural or synthetic biofilament proteins.

Regarding the type and structure of spider silk proteins which may be used in the present invention, it is referred to WO 2006008163 and WO 2006002853, which are incorporated herein by reference.

Preferably, the dope solution is at least 1%, 5%, 10%, 15% weight/volume (w/v) silk protein. More preferably, the dope solution is as much as 20%, 25%, 30%, 35%, 40%, 45%, or 50% w/v silk protein. In preferred embodiments, the dope solution contains substantially pure spider silk protein. In preferred embodiments, the dope has a pH of approximately 6.9.

By "dope solution" is meant any liquid mixture that contains silk protein and is amenable to extrusion for the formation of a biofilament or film casting. Dope solutions may also contain, in addition to protein monomers, higher order aggregates including, for example, dimers, trimers, and tetramers. Normally, dope solutions are aqueous solutions of pH 4.0-12.0 and having less than 40% organics or chaotropic agents (w/v). Preferably, the dope solutions do not contain any organic solvents or chaotropic agents, yet may include additives to enhance preservation, stability, or workability of the solution.

According to a further embodiment, the microfluidic device of the invention additionally comprises a storage means connected to a microfluidic channel, comprising a solution of one or more substances selected from the group consisting of polypeptides, polysaccharides, marker molecules, quantum dots, metals, nucleic acids, lipids and low molecular drugs.

In a preferred embodiment, the diameter of the microfluidic channels is narrowing in the direction from inlet to outlet port.

A second aspect of the invention pertains to method for assembling spider silk proteins, comprising the steps of:
a) providing a microfluidic device as defined above;
b) controllably flowing fluids through the microfluidic channels by suitable means, thereby providing a laminar flow of said fluids after converging of said microfluidic channels; and thereby
c) aggregating said spider silk proteins.

In this method, the spider silk proteins are modified by substances selected from the group consisting of polypeptides, polysaccharides, marker molecules, quantum dots, metals, nucleic acids, lipids and low molecular drugs.

In a third aspect, an assembled protein, bead, sphere, microcapsule, fiber, thread, filament or nanofibril obtainable by the above method is provided.

Furthermore, the invention is directed to a paper product, textile, leather product, fabric, automotive cover and part, aircraft construction material, packaging material, electronic device, food product or pharmaceutical product comprising an assembled protein, bead, sphere, microcapsule, fiber, thread, filament as mentioned above. As an alternative aspect, the assembled protein, bead, sphere, microcapsule, fiber, thread, filament or nanofibril is present as a coating on said products.

Furthermore, the invention provides a skin care product comprising an assembled protein, bead, sphere, microcapsule, fiber, thread, filament or nanofibril as defined above in combination with keratin, cellulose, and/or collagen.

EXAMPLES

The proposed device/method possesses two main features:
Controllability Due to Laminar Flow By calculating the Reynold's number it can be shown, that the flow in a microfluidic device with a diameter in the order of 100 μm and with the flow-rates used is laminar. As a result no turbulent mixing between two neighboring liquid layers takes place. This makes it possible to let ions diffuse from the surrounding ionic solution into the protein-solution. With another experimental setup, ions could also be extracted from the inner channel by diffusion. In contrast to the aggregation-technique proposed by Liivak et at [5], in which the flow is rather turbulent, the border conditions and absolute concentrations of certain ions can be controlled in a much better way, due to an excellent predictability of diffusive mixing.

Combination of Application of Shear with Addition and Removal of Ions

Studies have shown that the phase separation and the assembly process of spider silk proteins (natural and recombinant) can be promoted by adding certain ions to the protein solution (phase separation) and by applying a shear force (alignment necessary for correct assembly). The proposed method allows the do both simultaneously.

Phosphate (like other lyotropic ions) is known to increase the surface tension of water and in this way promotes hydrophobic interactions [2]. Therefore it is very important to control the ion concentrations during the phase separation and assembly process. Applying microfluidics, concentrations of one or more ions can be specifically in- and decreased.

A second significant factor is the assurance of a shear due to an extensional flow. It is supposed that a flow induces orientation (alignment) of the involved proteins and therefore leads to a better interaction between the β-sheet forming polyalanine stretches of the primary structure of the silk proteins, which are assumed to be important for the stability of a thread [2].

Different Microfluidic Designs

The microfluidic devices can be build with more input channels at different positions. Narrowing inside the channels can mimic even closer the spider duct. Important is also the ability to build a 3D flow pattern, with which any contacts with the surfaces are omitted. Further, this set-up allows for the defined mixing of two or more different silk proteins in order to achieve a different physical or chemical stability of the resulting silk fibril, sphere or thread.

As described, the application of microfluidics unifies the possibility to control ion concentrations, to mix several different proteins, and to apply a shear force with controllability. Experiments as shown in the next paragraph have already provided evidence.

Figure 4:
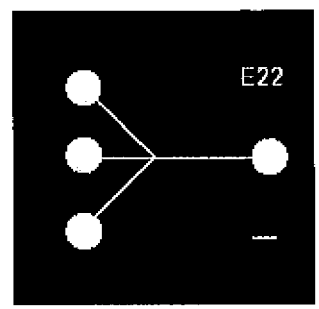
FIG. 4. CAD-layout of the channel design.

As both, the main components for experimental microfluidics and the bacterially produced silk proteins do already exist, the experimental setup is as follows:
Experimental Setup In the experimental setup typically micro-channels are used as shown in FIG. 4. The height is approximately 100 μm and the width of the main part of the channel 200 μm. Sealing the replica to a glass-slide irreversibly creates a microfluidic channel, which can be used for studies with a microscope, as shown in FIG. 5.

FIG. 4 shows the CAD-layout of the channel design. The main duct has a width of 200 μm. White components are part of the positive relief and form the channel.

Figure 5:
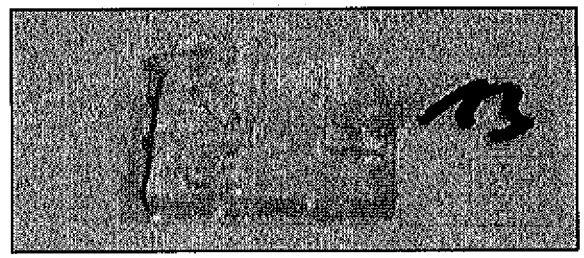
FIG. 5. A finished microfluidic device.

FIG. 5: Finished microfluidic device. Inlets and outlets were mould into the PDMS during curing. The fourth wall of the channel is a coverslide which enables the observation with a microscope.

Passivation of the Channels and Other Methods

One important step for the application of the proposed method is that the polymerization takes place in the lumen of the channel. Aggregation at the surfaces (PDMS and glass) causes unwanted side-effects. That is why the channel-surfaces were passivated with either BSA or by ultraviolet polymer grafting as described in [8] in detail. Better results could be achieved by building a three-dimensional microfluidic system: The inner flow (protein solution) was injected into the middle of the cross-sectional area with a 20 μm-micro needle from World Precision Instruments. Therefore the protein-flow is not in contact with neither the PDMS nor the glass-slide, as it is completely surrounded with the ionic solution, and aggregation at the surfaces does not take place.

This step seems to be very crucial for biomimicking the duct of a spider, in which the spinning dope is also separated from the epidermis of the duct by a thin film.

Results

For the performed experiments a fluidic channel was prepared as described above and filled as shown in FIG. 3. The $C_{16}$-concentration was 10 mg/ml and the ionic solution contained $NaH_2PO_4$ (and other phosphate ions such as $KH_2PO_4$, etc.) in water at a concentration of 1 mol/l. The flow was pumped with a syringe pump for Harvard Instruments at a rate of 0.2 to 1 µl/min per channel.

Figure 6:
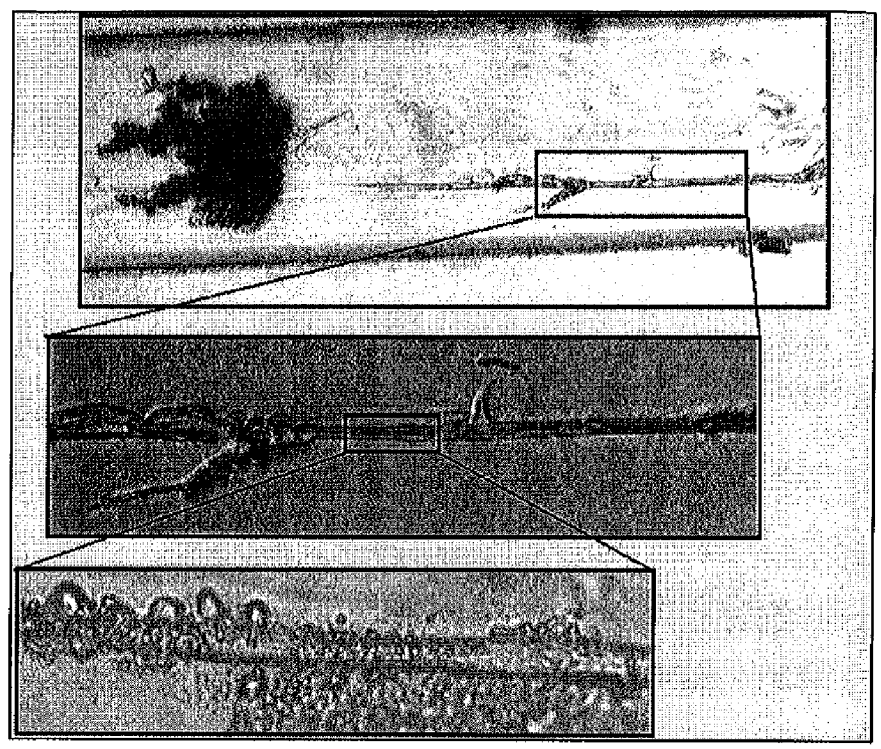
FIG. 6. Threads of protein $C_{16}$ formed in a micro-channel at the interface of PDMS at different resolutions.

It was possible to produce first threads in different constellations: FIG. 6 shows threads of protein $C_{16}$ formed in a micro-channel at the interface of PDMS at different resolutions. The Channel has a diameter of 100 µm.

Figure 7:
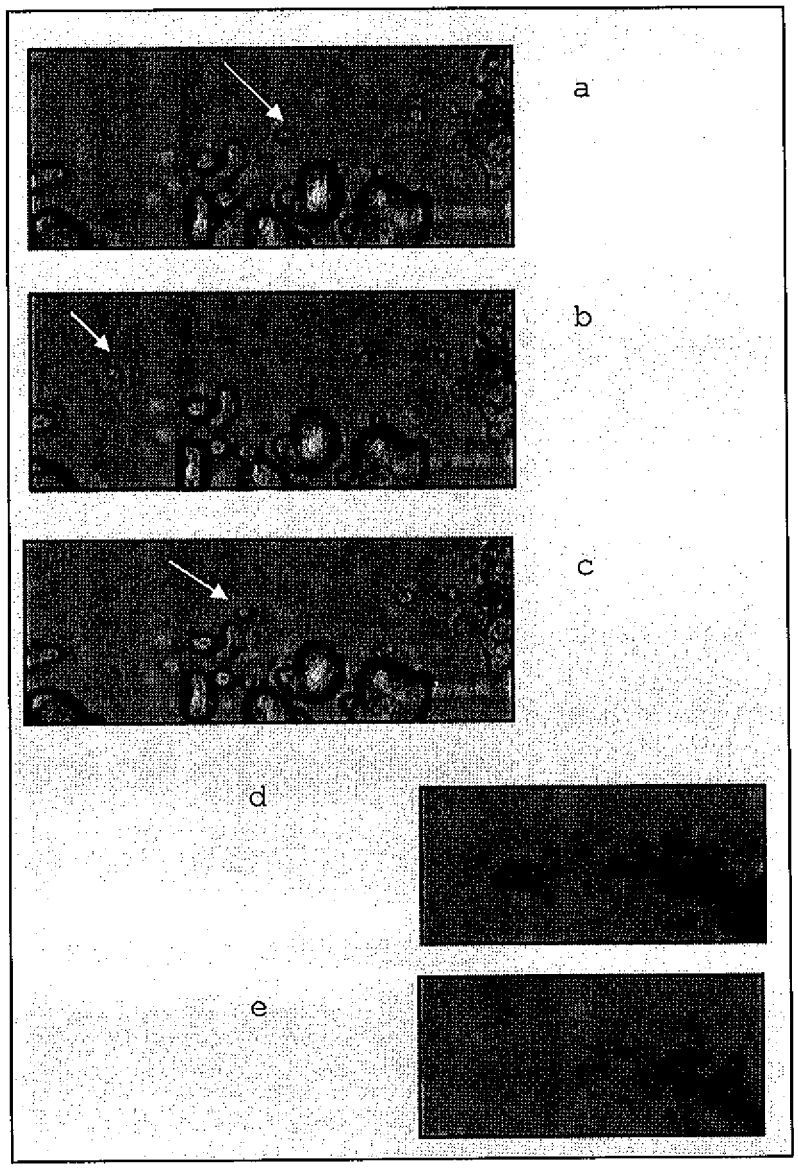
FIG. 7. A sequence of pictures taken when flow rate is increased step by step then decreased.

FIG. 7 is a sequence of pictures taken from one experiment. An aggregate (marked with an arrow) is hold in position by a thin thread in the lumen, which is not visible at the solution. The flow rate is increased step by step and the particle is drawn to the left due to the frictional force of the fluid. After the flow rate is decreased, the particle is pulled to the right by the thread.

Picture (d) and (e) show the excerpt of the aggregate where the invisible thread is detached during its breakaway. As the forces of the particle in the flow fails, the detachment jumps back.

Figure 8:
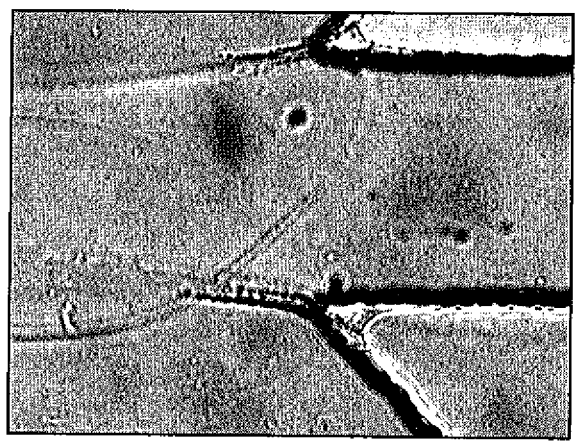
FIG. 8. Junction in the microfluidic device where the protein flow meets the flow of the NaH2PO4 solution.

The best indication for the success of the method is shown in FIG. 8.

FIG. 8 shows the junction in the microfluidic device, where the protein-flow meets the flow of the $NaH_2PO_4$-solution. In the area where phosphate-ions have diffused into the protein-solution and where mechanical stress is applied due to acceleration, the aggregation-process is pushed forward and the formation of thread-like structures can be observed.

Injection of protein by a micro needle as described above is very promising as indicated in picture 8 indicates. By injection into the volume without contact to the PDMS or glass surfaces, it is possible to create freely floating thread-like structures.

INDUSTRIAL APPLICATION

It is explicitly noted that the most preferred applications of the spider silk structures of the present invention are in the manufacture and processing of clothing fabric (textiles) and leather, automotive covers and parts, aircraft construction materials as well as in the manufacture and processing of paper.

The spider silk structures of the present invention may be added to cellulose and keratin and collagen products and thus, the present invention is also directed to a paper or a skin care and hair care product, comprising cellulose and/or keratin and/or collagen and the spider silk structures of the present invention. Papers and skin care and hair care products, in which the silk structures of the present invention are incorporated are showing improved characteristics, in particular improved tensile strength or tear strength.

Furthermore, the assembled spider silk structures of the invention may be used as a coating for textile and leather products, thereby conferring stability and durability to the coated product. The silk structures in particular show applicability for coating leather products, since in this case, tanning and its negative effects for environment can be avoided or at least be reduced.

They can also be used in food packaging or electronic devices, for example in batteries. Experiments conducted with films made out of the modified spider silk proteins showed their resistance and stability towards acidic pH after immersion in battery acid.

The invention provides a pharmaceutical or cosmetical composition containing a spider silk structure as obtained by the hereinabove mentioned method and a pharmaceutically acceptable carrier.

REFERENCES

1. Seidel A, Liivak O, Jelinski L W. (1998) Artificial spinning of spider silk MACROMOLECULES 31 (19): 6733-6736
2. Scheibel, T. (2005) Protein fibers as performance proteins: new technologies and applications. Curr. Opin. Biotech. 16, 427-433 zusätzlich: T. Scheibel: Microb. Cell Fact. 3, 14 (2004)
3. Hümmerich, D., Helsen, C. W., Oschmann, J., Rudolph, R. & Scheibel, T. (2004) Primary structure elements of dragline silks and their contribution to protein solubility and assembly, *Biochemistry* 43, 13604-13612
4. Hümmerich, D., Ackerschott, C. & Scheibel, T. (2004) Recombinant spider silk proteins. WO 2006/008163;
5. Liivak, O. et al. (1998) A micro fabricated wet-spinning apparatus to spin fibers of Silk Proteins, *Macromolecules* 31, 2947-2941
6. McDonald J C, Duffy D C, Anderson J R, Chiu D T, Wu H, Schueller O J A, Whitesides G M. (2000) Fabrication of microfluidics systems in poly(dimethylsiloxan). *Electrophoresis* 21, 27-40
7. F. Vollrath & D. P. Knight. (2001) Liquid crystalline spinning of spider silk. Nature 410, 541-548
8. Hu S W, Ren X Q, Bachman M, et al. (2004) Surface-directed, graft polymerization within microfluidic channels. ANALYTICAL CHEMISTRY 76 (7): 1865-1870
9. Gosline J M, Guerette P A, Ortlepp C S & K. N. Savage. (1999) THE MECHANICAL DESIGN OF SPIDER SILKS: FROM FIBROIN SEQUENCE TO MECHANICAL FUNCTION, Journal of Experimental Biology 202, 3295-3303

What is claimed is:

1. A microfluidic device comprising:
   a) at least three microfluidic channels formed in said device comprising fluids flowing therethrough, wherein the channels converge in said microfluidic device to one combined channel in order to provide a laminar flow of said fluids, said combined channel leading to an outlet port;
   b) at least three inlet ports formed in said device to permit access to the at least three microfluidic channels; and
   c) at least three fluid storage means, each being connected via said inlet ports to one of the at least three microfluidic channels, characterized in that at least one of said storage means comprises a solution of one or more spider silk proteins and at least one of said storage means comprises an ionic solution comprising potassium and phosphate ions.

2. The microfluidic device of claim 1, wherein the solution of one or more spider silk proteins comprises authentic or synthetic spider silk proteins.

3. The microfluidic device of claim 1, which additionally comprises a storage means connected to a microfluidic channel, comprising a solution of one or more substances selected from the group consisting of polypeptides, polysaccharides, marker molecules, quantum dots, metals, nucleic acids, lipids and low molecular drugs.

4. The microfluidic device of claim 1, wherein the diameter of the microfluidic channels is narrowing in the direction from inlet to outlet port.

5. A method for assembling spider silk, comprising the steps of:
   a) providing a microfluidic device according to claim 1;
   b) controllably flowing fluids through the microfluidic channels by suitable means, thereby providing a laminar flow of said fluids after converging of said microfluidic channels; and thereby
   c) aggregating said spider silk proteins.

6. The method of claim 5, wherein the spider silk proteins are modified by substances selected from the group consisting of polypeptides, polysaccharides, marker molecules, quantum dots, metals, nucleic acids, lipids and low molecular drugs.

* * * * *